United States Patent [19]

Varterasian et al.

[11] Patent Number: 5,253,528
[45] Date of Patent: Oct. 19, 1993

[54] VIBRATION TECHNIQUE FOR MEASURING BONDING IN AUTOMOTIVE RADIATORS

[75] Inventors: John H. Varterasian, Livonia; Francis H. Chen, Rochester Hills; Wolfgang Kiel, Warren, all of Mich.; Kent E. Brittin, Lockport, N.Y.; Patrick D. Quinn, Rochester Hills, Mich.; Kenneth J. Zielesch, Fraser, Mich.; Kurt A. Tesnow, Sterling Heights, Mich.; Thomas H. Worswick, Mount Clemens, Mich.

[73] Assignee: General Motors Corporation, Detroit, Mich.

[21] Appl. No.: 716,494

[22] Filed: Jun. 17, 1991

[51] Int. Cl.$^5$ .................................. G01H 13/000
[52] U.S. Cl. ........................................ 73/582
[58] Field of Search .................. 73/582, 579; 165/11.1

[56] References Cited

U.S. PATENT DOCUMENTS 2,486,984 11/1949 Rowe ................................. 73/582
3,355,933 12/1967 Rowe ................................. 73/579
3,815,407 6/1974 Lavery ............................... 73/582
3,857,279 12/1974 Salzer et al. ...................... 73/582
4,287,766 9/1981 Ensminger ......................... 73/582

Primary Examiner—Hezron E. Williams
Assistant Examiner—Nashmiya Ashraf
Attorney, Agent, or Firm—Ronald L. Phillips

[57] ABSTRACT

Nondestructive testing of heat exchangers (12), such as a radiator, measures the percentage of good bonds between air centers and cooling tubes based on natural or resonant frequencies of the exchanger (12). The exchanger (12) is excited by an audio speaker (38) and measured for a first natural frequency in the center thereof by an accelerometer (44). The natural frequency is indicative of the percentage of good bonds in the center portion of the exchanger (12) based on the stiffness thereof. The audio speaker (38) is moved to an antinode of a higher frequency mode to measure a second natural frequency indicating the percentage of bonds at the edges and corners thereof. The resonant frequencies are compared to standards to determine the actual percentage of good bonds.

17 Claims, 6 Drawing Sheets

VIBRATION TECHNIQUE FOR MEASURING BONDING IN AUTOMOTIVE RADIATORS

TECHNICAL FIELD

The invention relates to a method and apparatus for testing the vibration characteristics of a heat exchanger, and more particularly, for measuring the quality of the bonding of air centers to the coolant tubes of automotive radiator cores.

BACKGROUND OF THE INVENTION

Automotive heat exchanger cores, such as aluminum radiator cores, are produced by heating a core assembly to bond the air centers to the cooling tubes. Bonding of the air centers results when the core assembly is placed in a vacuum furnace and the cladding material on the tubes melts and brazes the air centers to the tubes. For maximum heat transfer and radiator efficiency, the bonds should result evenly along the width of the cooling tubes where the air centers contact the cooling tubes. However, problems can occur during the manufacturing process that lead to missing bonds, or bonds that are only partially formed. These problems could be due to variations in furnace thermal controls, material inconsistencies, tube and air-center forming problems upstream from the brazing process, etc.

Samples of radiator cores are manually inspected after the brazing process to verify that sufficient bonding did occur. This destructive inspection method requires the sawing or sectioning of cores. The sectioned core is then spread apart for visual inspection. A poor bond is evidenced by the lack of a fillet or ridge of bonding material on the cooling tube. A batch of radiators is determined to be acceptable or unacceptable dependent on the percentage of poor bonds of the destroyed samples. As a destructive inspection technique, the procedure is not only costly, because cores are destroyed, but it is also not reliable. As a manual inspection method, this current procedure is time consuming and labor intensive.

Non-destructive vibration techniques have been known to sample other types of structural members. Exemplary of this technique is U.S. Pat. No. 3,355,933, issued Dec. 5, 1967 to Rowe. The patent discloses a vibration apparatus for testing articles wherein the article is vibrated and a determination of the natural frequency of the article is made by sensing sound waves. The natural frequency is indicative of the relative grade of such articles. Different articles vibrating in identical modes have the same number of nodes of vibration and the same number of antinodes. Therefore, the frequency response in the occurrence at the natural frequencies is compared to known grades to determine which grade being tested the article falls in.

U.S. Pat. No. 4,287,766, issued Sep. 8, 1981 in the name of Ensminger discloses a method of detection of unacceptable solder joints by applying an acoustic vibration over the range of frequencies of the solder joints and observing the acoustic impedance of the joint. The frequency response is compared to a standard spectral response of known acceptable and unacceptable soldered joints which is used to determine whether the solder joint is acceptable or unacceptable. The occurrence of resonant frequencies and the amplitude thereof are compared to the standards for a qualitative determination of acceptability.

SUMMARY OF THE INVENTION

The invention is a method and apparatus for measuring defective bonding within core heat exchangers. The invention includes vibrating the core heat exchanger at a plurality of frequencies causing deflection of the heat exchanger as a whole, measuring a natural frequency of vibration of the core heat exchanger at a mode of vibration, and comparing the natural frequency to predetermined frequencies to determine the amount of defective bonding in the core heat exchanger. Also included is measuring a second natural frequency at a second mode of vibration, and comparison thereof to predetermined frequencies. The two modes are indicative of bonding in different regions of the heat exchanger core.

BRIEF DESCRIPTION OF THE DRAWINGS

Advantages of the invention will be better understood by reference to the detailed drawings wherein.

DESCRIPTION OF THE PREFERRED EMBODIMENT

Figure 1:
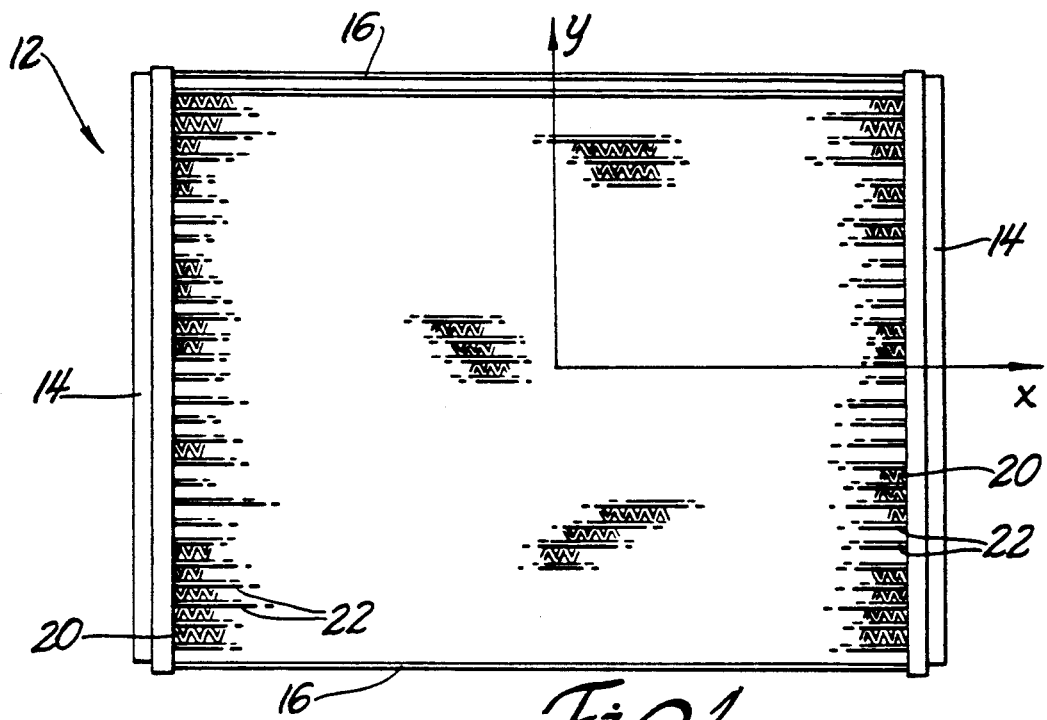
FIG. 1 is a front view of a typical radiator core.
Figure 2:
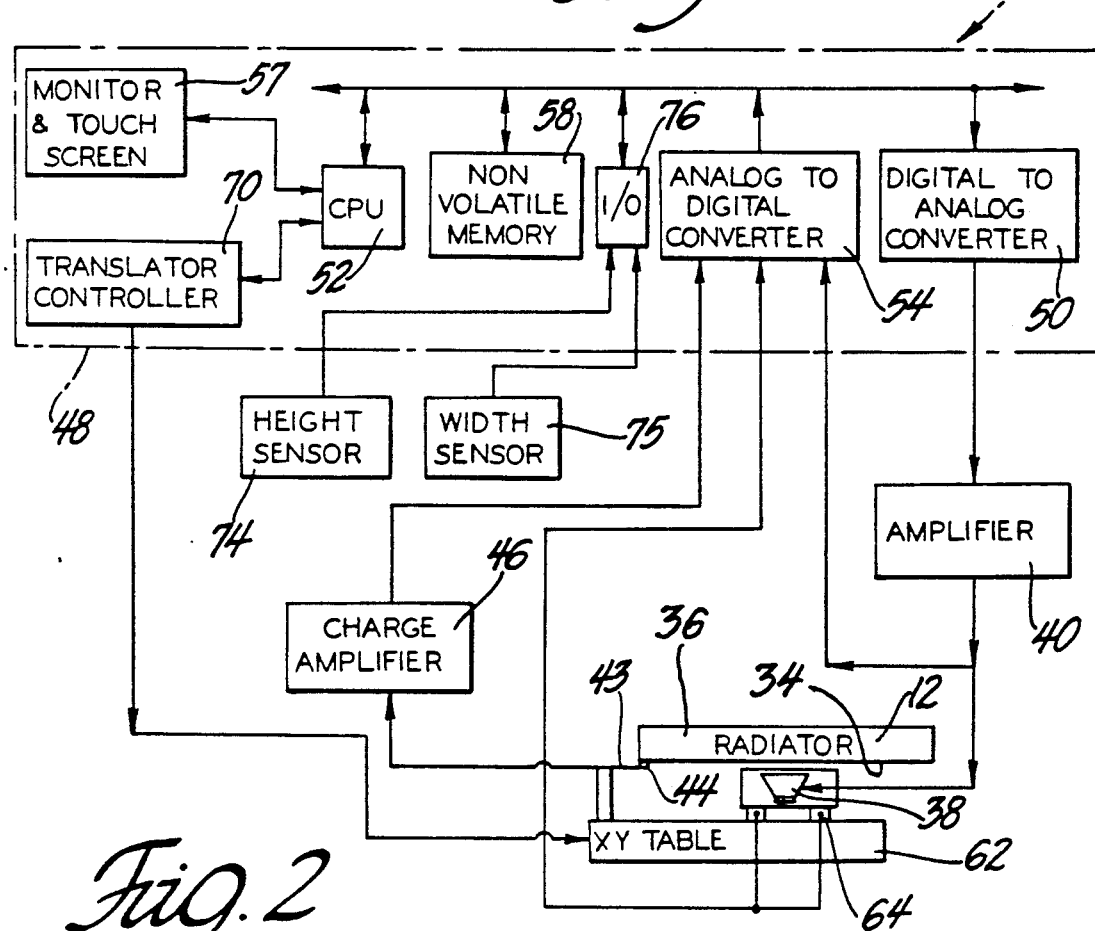
FIG. 2 is a block diagram of the subject invention.

A measuring assembly for measuring defective bonding within heat exchanger cores 12 is generally illustrated at 10 in FIG. 2. In the preferred embodiment, the heat exchanger core 12 is an aluminum radiator as generally illustrated in FIG. 1.

Figure 3:
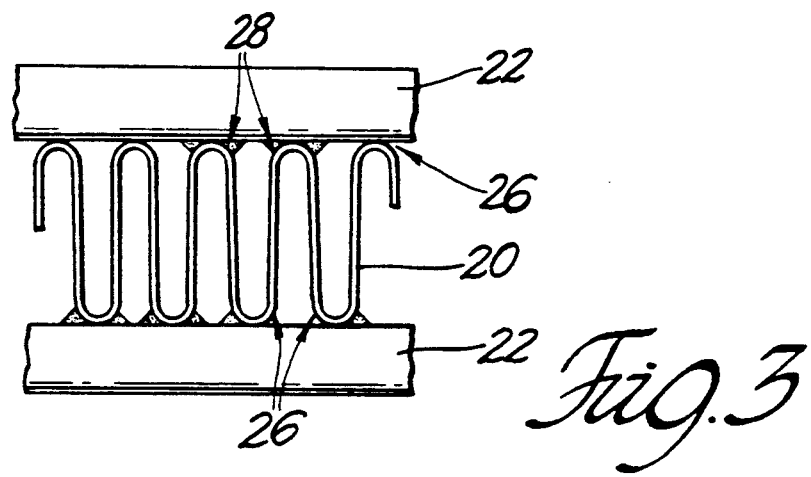
FIG. 3 illustrates an enlarged section of FIG. 1 having partial bonding.

As illustrated in FIG. 1, the heat exchanger or radiator core 12 includes headers 14 and reinforcement members 16 for providing a generally rectangular structure of the radiator core 12. Also included are air centers 20 and coolant tubes 22 which are ideally bonded to one another. Examples of occurrences of no bonds between the coolant tubes 22 and air centers 20 are indicated at 26 in FIG. 3. Examples of the occurrences of bonding between the air centers 20 and the coolant tubes 22 are indicated at 28 in FIG. 3. Therefore, the number of bonds 28 and the number of defective bonds 26 in the radiator core 12 are determined for establishing whether the radiator core 12 is acceptable or unacceptable.

The theoretical basis for the vibration technique for measuring the degree of bonding in radiator cores 12 is that any structure possesses natural modes of vibration at specific frequencies given by:

$$f_n \propto \sqrt{k/m}$$

where k equals stiffness of the structure, m equals mass of the structure, and n equals 1, 2, 3 . . . denotes the various modes of vibration.

Since a radiator core 12 is a structure with the major structural elements joined together by bonding, this equation is applicable. Moreover, since radiator core 12 stiffness is basically due to the bonding, defective bonding will reduce the structural stiffness with very little or no change in mass. Thus, the natural frequencies, $f_n$, are directly proportional to the square root of the stiffness, i.e., $$f_n \propto \sqrt{k}$$

If a radiator core 12 has defective bonds, its stiffness will be lower than a perfectly bonded core 12 and correspondingly lower natural frequencies will result. Therefore, values of the natural frequencies of a radiator core 12 provide a nondestructive measure of the degree of bonding in the core. The equations hold for any brazed structure of similar configuration. Therefore, this method also applies to other heat exchanger products such as copper brass radiators, heater cores, oil coolers, evaporators, condensers, etc.

A radiator core 12 has many natural frequencies or modes of vibration. Each mode has an associated mode shape, i.e., the naturally preferred deflection shape, which is a function of the radiator core 12 configuration and the distribution of mass and stiffness throughout the core 12. At different natural frequencies, different regions of a radiator core 12 undergo vibration. Therefore, each of the natural frequencies have different sensitivies to local stiffness changes due to defective bonds 26 and different regions. Thus, even though measuring one of the natural frequencies is usually sufficient to indicate good or bad bonding, measuring two or more modes makes the technique more effective. The entire heat exchanger core 12 is excited which causes deflection of the whole.

For purposes of diagnosing radiator unbonding, any mode which is sensitive to the effects of poor bonding could be monitored. It is more effective to monitor lower frequency modes than higher frequency modes because the frequencies of higher modes are more dependent on small build differences which will make it difficult to establish a consistent baseline frequency for reference. The five lowest frequency out-of-plane bending modes are: SS-1, first symmetric-symmetric mode; SS-2, second symmetric-symmetric mode; AS-1, first anti-symmetric mode; AS-2, second anti-symmetric mode; and SS-3, third symmetric-symmetric mode where the notations refer to symmetry about the X and Y axes respectively.

Figure 4:
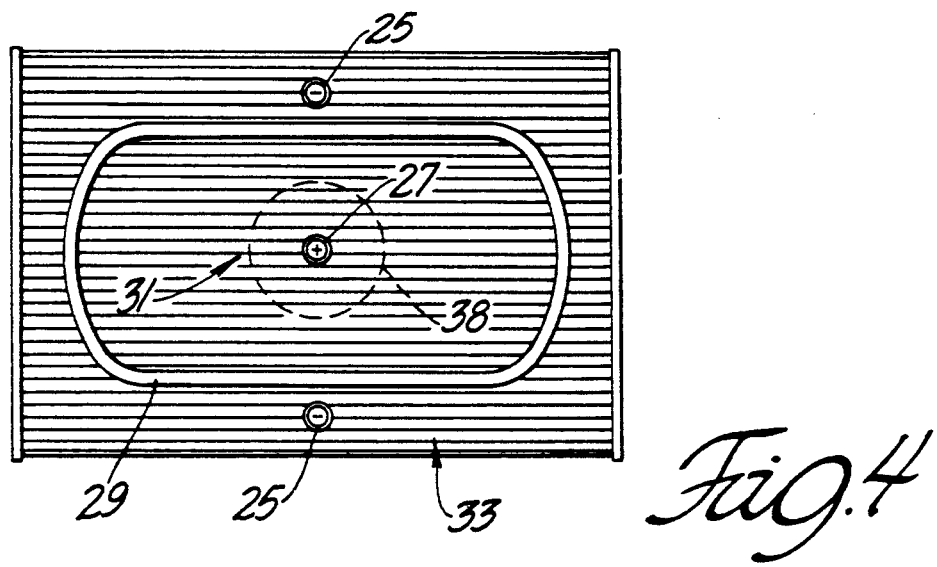
FIG. 4 illustrates the mode shape of a first natural frequency of the radiator.
Figure 5:
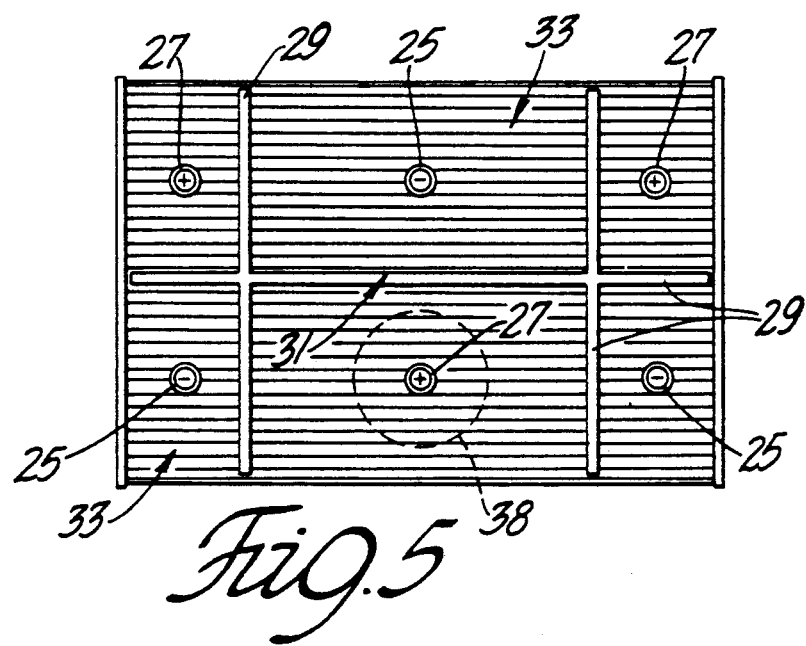
FIG. 5 illustrates the mode shape of a second natural frequency of the radiator.

For example, the mode shapes of two of the modes for a typical radiator are illustrated in FIGS. 4-5. The "−" sign 25 indicates the areas of the core 12 which deflect in a direction opposite to the areas with the "+" sign 27, and the solid lines 29 are nodal lines where no vibrations occur.

For the radiator core 12 illustrated in FIG. 1, the first symmetric-symmetric bending mode, SS-1, illustrated in FIG. 4, is most sensitive to poor bonds near the center 31 of the radiator core 12 since there is significant bending in this region. However, since there is only small bending near the edges or corners 33, the natural frequency of the SS-1 mode is less affected by poor bonds 26 in these corner and edge regions 33. The first antisymmetric-symmetric mode, AS-1, is illustrated in FIG. 5 and has higher bending deflections near the corners and edges 33 and will be more sensitive to defective bonds 26 at the corners and edges 33, and less sensitive at the center 31 of the radiator core 12. Unbondings at the sides and corners mainly affect the stiffnesses close to the nodal lines of SS-1, AS-1, and AS-2 modes. There should be little change in the modal frequencies of the SS-2 mode since the stiffness of this mode is mainly due to the stiffness of the coolant tubes 22 which are not affected by unbonded regions in the air centers 20. Thus, by monitoring two selected modal frequencies, not only is it possible to distinguish between a good radiator core 12 and a defective radiator core 12, but it is also possible to gain information on the distribution of the defective bonds 26.

For radiators of other configurations, two modes of vibration other than the SS-1 and AS-1 modes may be better for measuring the bonding of the total radiator core 12. Before bond quality measurements can proceed, it is necessary to determine the natural frequencies of the two selected modes of a radiator core with 100% bonding. This establishes a reference for comparison purposes. These values may be determined by use of finite element models or by testing a known good core.

In order to establish standard or reference frequencies associated with percentage of bonding, a radiator core is tested having 100% bonding. The first and second modal frequencies of a radiator core 12 having 100% bonding is measured. Thereafter, bonds are removed and the radiator core 12 is tested to indicate decreasing percentages of good bonds associated with a resonant or natural frequency by successively removing bonds. The bonds 28 may be removed by poking, sawing, drilling, etc., out the bonds 28. This process may be continued down to any frequency or bond percentage desired. This production of a reference frequency percent bonding list will be produced for each type of radiator core 12 for the AS-1 and SS-1 modes. The radiator type may be identified by part number or a combination of length, width and weight.

Figure 8:
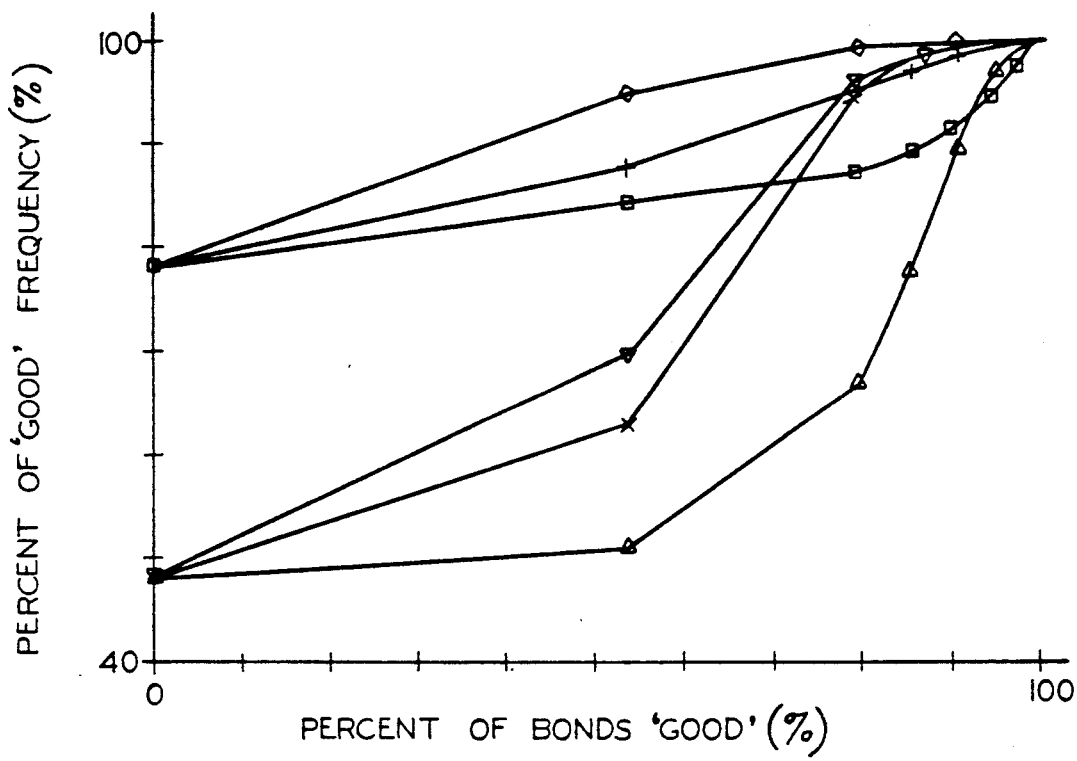
FIG. 8 is a chart of frequency percentage versus bonding percentage.

The curves of FIGS. 8 indicate a sensitivity of frequencies to percentage of good bonds. The horizontal axis is in terms of percentage of good bonds and the vertical axis is the percentage of the unbonded frequency referenced to the perfectly-bonded frequency. The lines with the squares indicate the SS-1 mode sensitivity at the center of the core 12. The "+" indicate the SS-1 mode sensitivity at the sides and the diamond indicates the SS-1 mode sensitivity at the corner. With regard to the AS-1 mode, the upright triangle indicates sensitivity at the center, the "X" indicates sensitivity at the side, and the upside down triangle indicates sensitivity at the corner.

In order to test and measure acceptability, a radiator core 12 is placed in a horizontal plane through the X-Y axis and is supported by a test frame 35. A first face 34 of the radiator core 12 is oriented in a downward direction as illustrated in FIG. 2, and a second face 36 is oriented in an upward direction. The measuring assembly 10 includes acoustic means 38 for exciting the radiator core 12 at a plurality of frequencies. The acoustic means 38 comprises an audio speaker adapted to be operatively connected below the first face 34 of the radiator core 12 for producing acoustical energy directed toward radiator core 12. The radiator core 12 will vibrate during application of the acoustical energy. An audio amplifier 40 is connected to and drives the audio speaker 38 by receiving a sine wave signal and producing a driving signal to the speaker 38, as commonly known in the art.

The assembly 10 includes sensing means in contact with the radiator core 12 for measuring the frequency of vibration of the radiator core 12. The sensing means includes an accelerometer 44 mounted on a flexible spring 43 with its base contacting the first face 34 of the radiator core 12 for measuring the vibration frequency of the radiator core 12 producing a sensed signal indicative thereof. The accelerometer 44 is an instrument used to sense accelerations and convert them into corresponding electrical quantities and may be any commercially available accelerometer. The sensing means also includes a charge amplifier 46 for amplifying the sensed signal producing a measurement signal.

The use of acoustical, or proximity, excitation has several advantages over the conventional method of shaker excitation which requires a mechanical connection of a shaker to the radiator core 12. The test is faster since no time is required for mechanical connection. The measurement is highly repeatable since the acoustic coupling is not subject to the variations that can occur in a mechanical attachment. The accelerometer 44 contacts the radiator core 12 in a repeatable manner which is necessary to achieve a repeatable bond measuring system.

To maximize the signal to noise ratio of the measurement signal, the location of the audio speaker 38 is usually different for the two selected modes of vibration. The general rule is to locate the audio speaker 38 directly below the maximum modal deformation. For instance, when searching for the symmetric-symmetric SS-1 mode of a particular radiator core 12, the optimum location of the audio speaker 38 is at the center of the radiator core 12, as indicated in FIG. 4. For the antisymmetric-symmetric AS-1 mode, the optimum is about one quarter of the width (Y axis) and one half of the length (X axis) of the radiator core 12, as indicated in FIG. 5. The accelerometer 44 is ideally located at one of the antinodes of the mode.

The movement and positioning of the audio speaker 38 and accelerometer 44, and the measurement of signals and the relative phase may be manually accomplished for the measurement thereof, or alternatively automated as subsequently explained.

Figure 7A:
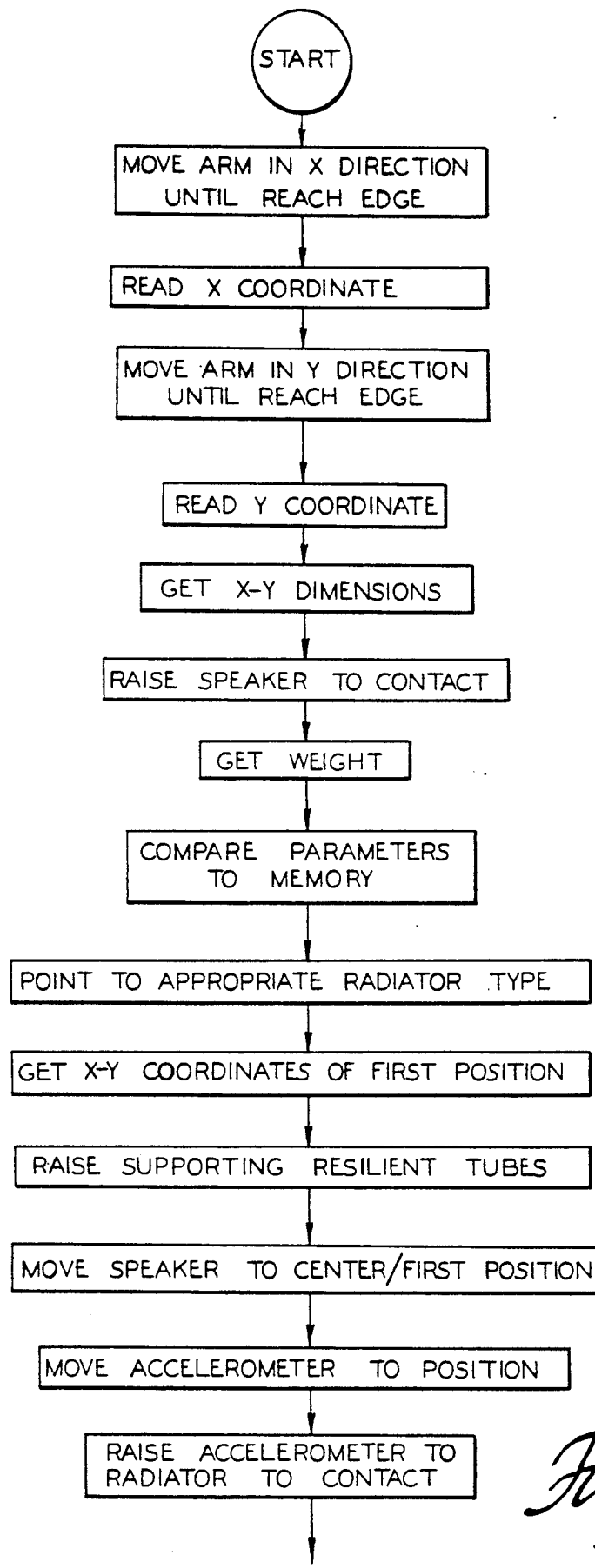
FIGS. 7a and 7b are flowcharts of the processor means.
Figure 7B:
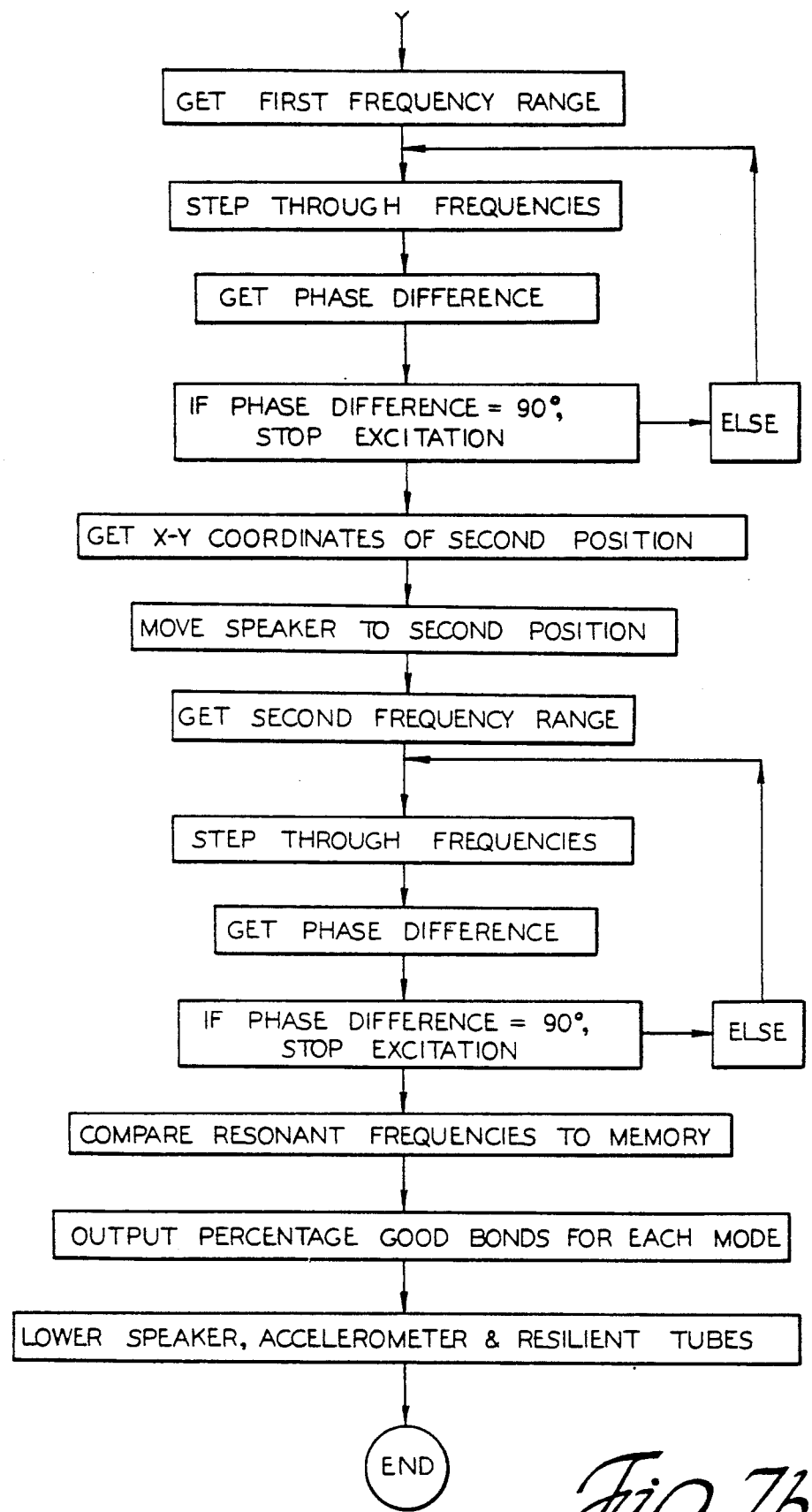

The assembly 10 includes controller means 48 for implementing automation and measurement of the amount of defective bonding in the radiator core 12. The controller means 48 includes processor means 52 for controlling the excitation and measurement. The processor means 52 may be comprised of a commonly available central processing unit (CPU). The processor 52 operates under the control of a control program stored therein which operates according to the flowchart in FIGS. 7a-b. The processor 52 produces the driving signal, receives the measurement signal, determines the occurrence of the natural frequencies, and controls positioning of the audio speaker 38 and accelerometer 44. The processor means 52 outputs digital sine wave signals in a series of frequency steps within a predetermined range of frequencies, within which range the natural frequency indicating 100% bonding will occur.

The controller means 48 also includes a digital to analog converter 50 for producing a single frequency analog sine wave signal to the audio amplifier 40 for driving the audio speaker 38 to vibrate the radiator core 12. The digital to analog converter 50 receives the digital sine wave signals from the processor 52 and convert same to the analog signal.

The controller means 48 includes an analog to digital converter 54 for digitizing the analog sine wave signal and the measurement signal producing a digitized sine wave signal and digitized measurement signal. The processor 52 receives these signals and may then determine the phase relationship and identify resonant frequency at a 90° phase difference.

The controller means 48 include programmable memory means 58 for storing information regarding each particular radiator core type to be measured. The programmable memory means 58 stores a part number designation indicative of radiator core type, and associated with each type, the following is stored: length and width measurements of the particular radiator including allowed tolerance ranges, weight including allowed tolerance range, first and second sensor locations, frequency range about the first natural frequency, frequency range about the second natural frequency the X-Y coordinates of the first and second locations of the speaker 38, the X coordinate of the accelerometer 44, and a listing and correlation of resonant frequencies and percent good bonds associated therewith.

A monitor and touch screen 57 allows initiation of the control program and receives the resonant or natural frequency identified by the processor means 52 to visually display the test results of whether or not the radiator passed or failed, and frequency and percentage bonding at each mode.

The processor means 52 receives and processes the information stored in the memory means 58 and controls the positioning of the audio speaker 38 and accelerometer 44 based on the dimensions of the radiator core 12, and controls the monitor and touch screen 57 to indicate the percentage of good or bad bonds based on the sensed resonant frequency.

The assembly 10 includes an X-Y translation table 62 and translation controller 70 shown in FIG. 2, for supporting and positioning the audio speaker 38 and the accelerometer 44. The table 62 includes linear actuators 80, 82 for moving the audio speaker 38 in the X and Y directions originating from reference zero point R in the corner of the table 62 and radiator 12. Initially, the processor means 52 determines the dimension from the selected radiator 12 by instructing sensors described below, to follow the header 14 and then the reinforcement member 16 extending from the reference corner R to obtain Y and X length measurements, respectively. The arms 72, 73 include width and length sensors 74, 75 for sensing the arrival at the edge of the header 14 and the edge of the reinforcement member 16. The sensors 74, 75 may be photo cells. The sensors 74, 75 produce width and length signals, respectively, which are transmitted to an input/output device 76 of the controller means 48 for transmission to the processor means 52.

Figure 6:
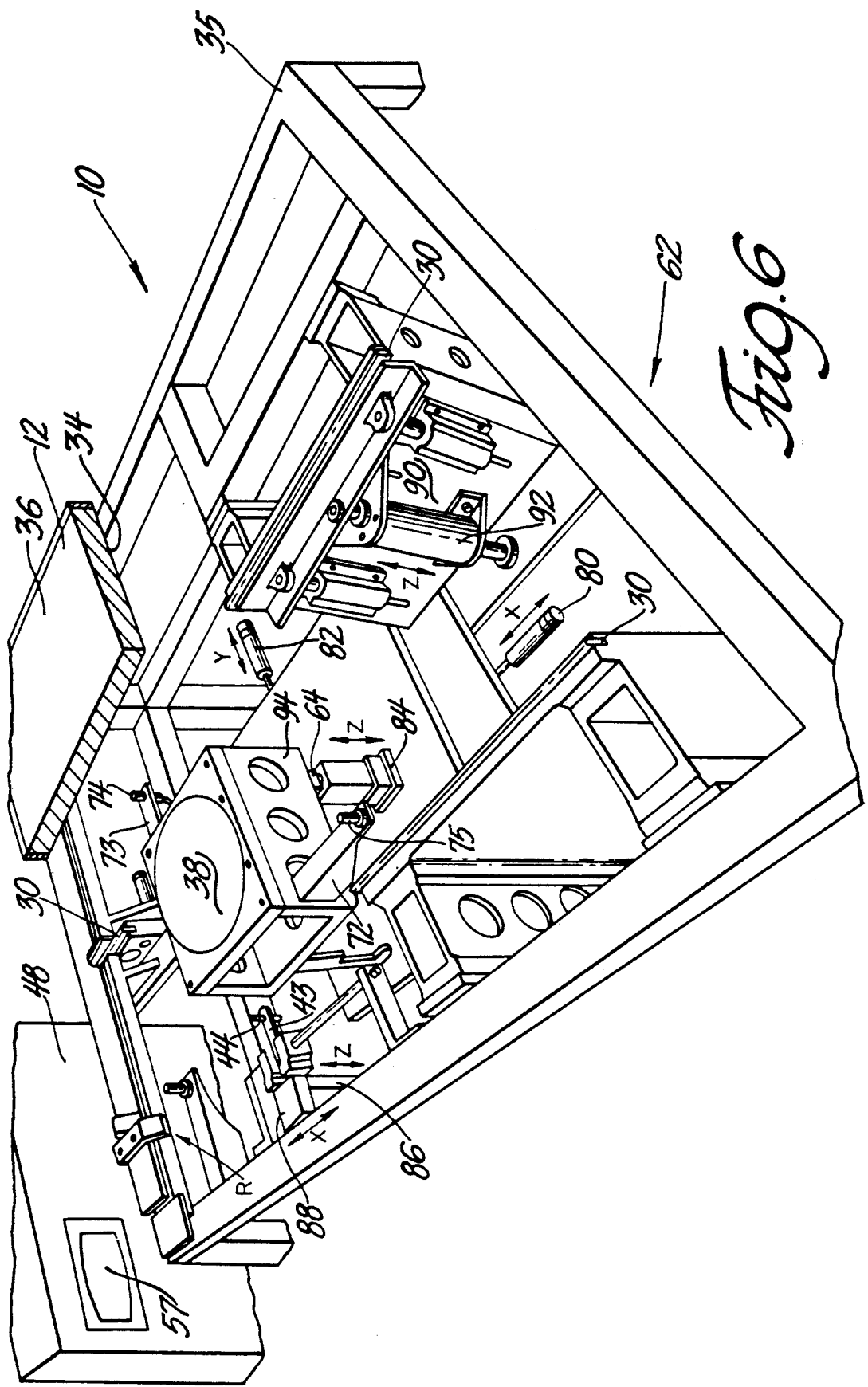
FIG. 6 illustrates an automated set-up of FIG. 2.

The audio speaker 38 is contained within a speaker housing 94. The X-Y table 62 includes load cells 64 for measuring the weight of the radiator 12. The load cells 64 are connected on the bottom portion of the speaker housing 94. The translator controller 70 receives a speaker and accelerometer coordinate signal to control the X-Y translation table 62 for movement of the audio speaker 38 and accelerometer 44, respectively, to the specified locations. The X and Y coordinates of the audio speaker 38 are obtained by controlling the linear actuators 80, 82, such as servomotors, solenoids, etc., as commonly known in the art. Pneumatic valves 84 adjust the height of the audio speaker 38 in the Z direction. The accelerometer 44 is moved only in the X and Z directions. A linear actuator 86 as with the audio speaker 38, moves the accelerometer 44 in the X direction, and a vertical pneumatic cylinder 88 is connected to and moves the accelerometer 44 and the flexible spring 43 into and out of contact with the first face 34. The illustration of the X-Y translation table 62 in FIG. 6 is exemplary of such a device. Resilient means 30 is connected to a plate 90 which is height adjustable in the Z direction by pneumatic cylinders 92. The resilient means 30 comprises generally rubber or plastic tubing for allowing vibration of the core 12. Included are three sections of resilient tubing for supporting the core 12 at three locations.

The processor means 52 receives the X and Y lengths and the weight measurement from the load cells 64, and compares same with the memory means 58 to identify the radiator core type, and points thereto for the subsequent retrieval of data regarding the frequency ranges for vibration and the correlation between the natural frequencies and percent good/bad bonds. The translation controller 70 receives the X-Y coordinates of the speaker 38 and X coordinate of the accelerometer 44 from the processor means 52 and transmits same to the X-Y translation table 62 for movement of the audio speaker 38 and accelerometer 44 thereto. Upon arrival at the specified location, the X-Y translation table 62 transmits an acknowledge signal to control means 60. The processor means 52 in turn produces a vertical signal to the resilient vertical pneumatic cylinder 92 for raising of the resilient tubing 30 to raise the core 12 above and off the test frame 35 and to the vertical pneumatic cylinder 84 for movement of the accelerometer 44 against the radiator core 12.

The controller means 48 operates each component means for sequential operation thereof according to the flowchart illustrated in FIG. 7. With regard to general operation, the core 12 to be tested is placed horizontally on the test frame 35. The start command is depressed by the operator on the screen 57 and the processor means 52 commands the XY translation table 62 to determine the dimensions of the radiator core 12. The XY translation table 62 moves its arms from the reference point R along the X axis and then along the Y axis to the edges thereof, and the sensors produce signals upon reaching the edges. The width and length signals are transmitted to the processor means 52 through I/O 76. The processor means 52 then instructs the load cells 64 for measurement of radiator core 12. The speaker housing 94 is raised and moved into substantial supporting engagement with the radiator 12, and the load cells 64 produce a weight signal indicative of the weight thereof. The processor means 52 compares the length and width measurements and the weight signal to the standard radiator types stored in the memory 58. Upon matching of the measurements and the weight, the processor means 52 points to the particular radiator type in memory 58 and commands the translation controller 70 to position the audio speaker 38. The translation controller 70 obtains the coordinates from the processor means 52 associated with a radiator type and controls the XY translation table 62 to move the speaker 38 to the required position for the first mode of vibration. The resilient tubing 30 is first moved to raise the radiator core 12 out of contact with the speaker 38 and test frame 35, the speaker 38 is moved to the first position under the radiator core 12. The processor means 52 operates the pneumatic cylinders 92 (only one of which is shown) which raises the resilient tubing 30 to a position in contact with the first face 34 of the radiator core 12 to support the radiator 12 above the speaker 38. The audio speaker 38 is moved to the appropriate location, and the XY translation table 62 transmits an acknowledge signal to the processor means 52. The processor means 52 transmits the coordinate of the accelerometer 44 to the translation controller for positioning in the center of the radiator 12 along the reinforcement member 16. The processor means 52 thereafter produces the digital sine wave for excitation in the first mode. The processor means 52 obtains the first range of frequency from the memory 58 and steps through the range of frequencies, i.e., about a 70% to 110% range about the resonant frequency for perfect bonding wherein the change in frequency occurs at approximately one eighth of a Hertz, about every 30 to 40 milliseconds. The digital to analog converter 50 converts the digital sine signal to an analog sine wave signal to be amplified by the audio amplifier 40 and sent to the speaker 38.

When the audio speaker 38 is excited by the analog sine wave signal the acoustical energy causes the radiator core 12 to vibrate at the same frequency as the sine wave. The processor means 52 steps through a range of frequencies surrounding its expected resonant frequency for perfect bonding, and produces the sine wave signal for a predetermined time at each frequency. When frequency of the audio speaker 12 is excited at the core's natural frequency, the core 12 is at resonance and will vibrate at large relative amplitudes. This vibration is measured by the accelerometer 44. The measurement signal and the analog sine wave signal is received by the analog to digital converter 54 and sent to the processor means 52. For a lightly damped structure, such as a radiator core, the phase should be either plus or minus 90° degrees. Thus, the natural frequencies can be determined by stepping the frequency until a phase difference between the digitized measurement signal and the digitized sine wave is plus or minus 90°.

When the processor means 52 indicates plus or minus 90°, the natural frequency is stored in internal memory. Upon determining the first natural frequency, the processor means 52 moves the speaker 38 to the second location and the excitation is stepped into the vicinity of the second desired modal frequency. The same steps are used as in the first mode. The second natural frequency is stored in internal memory. After measurement completion, the speaker 38, accelerometer 44 and resilient tubing 30 are lowered to their initial positions allowing the core 12 to rest on the test housing 35.

Upon obtaining the natural frequencies at the SS-1 mode and the resonant frequency at the AS-1 mode, the frequencies are compared to the list of frequencies stored in the memory means 58. As long the percentage of good bonds is between 70% and 100%, the percentage of good bonds may be determined for this particular radiator core 12. The display means 57 will print out the percentage of good bonds and the frequencies associated therewith. A threshold value of a certain percentage is set for each mode, below which is indicated an unacceptable or non-passed core 12.

As a specific example, the measuring assembly was utilized on a radiator. It was found that the maximum SS-1 frequency was 305.7 Hz, and the maximum AS-1 frequency was 474.5 Hz. These frequencies represented 100% of the maximum frequency indicating no counts of defective bonds. A second radiator was tested which tested a SS-1 frequency of 303.1 indicating 99.2% of the maximum and the AS-1 frequency was measured at 473.0 indicating 99.7% of the maximum AS-1 frequency. This indicates an actual count of 51.5 bad bonds.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A method of measuring defective bonding within heat exchanger cores, the method including the steps of:
   vibrating the heat exchanger core at a plurality of frequencies causing deflection of the heat exchanger core as a whole;
   measuring a first natural frequency in a first mode of vibration indicative of bonding in a first region of the heat exchanger core;
   measuring a second natural frequency in a second mode of vibration indicative of bonding in a second region of the heat exchanger core;
   comparing the first and second natural frequencies to predetermined frequency values to determine the amount of defective bonding in the heat exchanger core.

2. A method as set forth in claim 1 further including producing acoustical energy directed toward the heat exchanger core in the first region of the heat exchanger core to produce the first mode of vibration.

3. A method as set forth in claim 2 further including producing acoustical energy directed toward the heat exchanger core in the second region of the heat exchanger core to produce the second mode of vibration.

4. A method as set forth in claim 3 further including measuring the vibration of the heat exchanger core and producing a sensed signal indicative thereof.

5. A method as set forth in claim 4 further including amplifying the sensed signal producing a measurement signal.

6. A method as set forth in claim 5 further including producing a stepped sine signal for producing the acoustical energy at a plurality of frequencies.

7. A method as set forth in claim 6 further including receiving the sine signal and the measurement signal to indicate whether the two are 90 degrees out of phase.

8. A method as set forth in claim 7 further characterized by measuring the first natural frequency value at a frequency range indicative of the first mode of vibration being of greater sensitivity to defective bonding at a center region than an edge region of the heat exchanger core.

9. A method as set forth in claim 8 further characterized by measuring the second natural frequency value at a frequency range indicative of the second mode of vibration being of greater sensitivity to defective bonding at the edge region than the center region of the heat exchanger core.

10. A measuring assembly for measuring defective bonding within heat exchanger cores, said assembly comprising:
    excitation means for vibrating the heat exchanger core at a plurality of frequencies causing deflection of the heat exchanger as a whole;
    sensing means operatively, connected to the heat exchanger core for measuring frequencies of vibration of the heat exchanger core at two different modes of vibration;
    controller means for receiving the frequencies of vibration and identifying a first natural frequency indicative of bonding in a first region of the heat exchanger core and a second natural frequency indicative of bonding in a second region of the heat exchanger core, and for comparing said natural frequencies to predetermined frequencies to determine the amount of defective bonding in the heat exchanger core.

11. An assembly as set forth in claim 10 wherein said excitation means comprises an audio speaker for receiving a sine wave signal and producing acoustical energy directed toward the heat exchanger core.

12. An assembly as set forth in claim 11 wherein said sensing means includes an accelerometer adapted to contact the heat exchanger core for measuring the vibration of the heat exchanger core and to produce a sensed signal indicative thereof.

13. An assembly as set forth in claim 12 wherein said sensing means includes a charge amplifier for amplifying said sensed signal for producing a measurement signal.

14. An assembly as set forth in claim 13 wherein controller means includes processor means for producing a digital sine signal, and for receiving said sensed signal to determine said natural frequencies.

15. An assembly as set forth in claim 14 wherein said controller means includes a digital to analog converter means for producing said analog sine wave signal.

16. An assembly as set forth in claim 15 further characterized by said controller means including memory means for storing heat exchanger core types with associated first and second region coordinates, and a listing of percentage good bonds correlated with measured natural frequencies.

17. An assembly as set forth in claim 16 further characterized by including translation means connected to and supporting said audio speaker and said accelerometer for automatically positioning said audio speaker to said first and second regions based upon said first and second region coordinates.

* * * * *